United States Patent
Ro et al.

(10) Patent No.: US 7,995,704 B2
(45) Date of Patent: Aug. 9, 2011

(54) PANORAMIC X-RAY PHOTOGRAPHING APPARATUS AND METHOD FOR PHOTOGRAPHING USING THE SAME

(75) Inventors: Chang Joon Ro, Seongnam-si (KR); Tae Woo Kim, Hwaseong-si (KR); Hyo Sung Cho, Wonju-si (KR); Sung il Choi, Wonju-si (KR)

(73) Assignees: Vatech Co., Ltd., Hwaseong-si, Gyeonggi-do (KR); Vatech Ewoo Holdings Co., Ltd., Yongin-si, Gyeonggi-do (KR)

( * ) Notice: Subject to any disclaimer, the term of this patent is extended or adjusted under 35 U.S.C. 154(b) by 119 days.

(21) Appl. No.: 12/448,255

(22) PCT Filed: Feb. 22, 2007

(86) PCT No.: PCT/KR2007/000932
§ 371 (c)(1),
(2), (4) Date: Jun. 15, 2009

(87) PCT Pub. No.: WO2008/072821
PCT Pub. Date: Jun. 19, 2008

(65) Prior Publication Data
US 2010/0054403 A1 Mar. 4, 2010

(30) Foreign Application Priority Data
Dec. 13, 2006 (KR) .................. 10-2006-0127179

(51) Int. Cl.
*A61B 6/14* (2006.01)
(52) U.S. Cl. ......................... 378/39; 378/197

(58) Field of Classification Search .............. 378/38–39, 378/196–198
See application file for complete search history.

(56) References Cited

U.S. PATENT DOCUMENTS

| 4,878,234 A | 10/1989 | Pfeiffer et al. |
| 4,907,251 A | 3/1990 | Mork et al. |
| 6,118,842 A | 9/2000 | Arai et al. |

(Continued)

FOREIGN PATENT DOCUMENTS

| EP | 0379331 | 7/1990 |
| EP | 1491145 | 12/2004 |

OTHER PUBLICATIONS

EP Search Report, mailed Nov. 15, 2010, of corresponding EP Patent Application No. 07709071.

(Continued)

*Primary Examiner* — Hoon Song
(74) *Attorney, Agent, or Firm* — The Nath Law Group; Jerald L. Meyer; Sungyeop Chung

(57) ABSTRACT

Disclosed herein is a panoramic X-ray photographing apparatus and a method for photographing using the same. The present invention relates to the panoramic X-ray photographing apparatus capable of conducting a panoramic photographing without generating X-ray in neck cervical vertebrae part employing a rotary arm driven in 3-axis direction. In case of scanning the neck cervical vertebrae part, a photographing can be conduct without X-ray. As a result, it is possible to prevent an image acquired by the neck cervical vertebrae part from being unclear. Also, an angle of incidence of X-ray at a photographing point can be controlled to be vertical, so that an image distortion phenomenon can be prevented. Furthermore, tempromandibular joint can be photographed at optimum enlargement ratio, thereby acquiring clear image.

21 Claims, 7 Drawing Sheets

U.S. PATENT DOCUMENTS

2004/0066877 A1 4/2004 Arai et al.
2004/0247069 A1* 12/2004 Arai et al. .................. 378/4
2005/0117696 A1 6/2005 Suzuki et al.
2006/0256921 A1 11/2006 Tachibana et al.

OTHER PUBLICATIONS

ISA/KR Search Report, mailed Sep. 14, 2007, of corresponding PCT/KR2007/000932.

* cited by examiner

[Fig. 1]
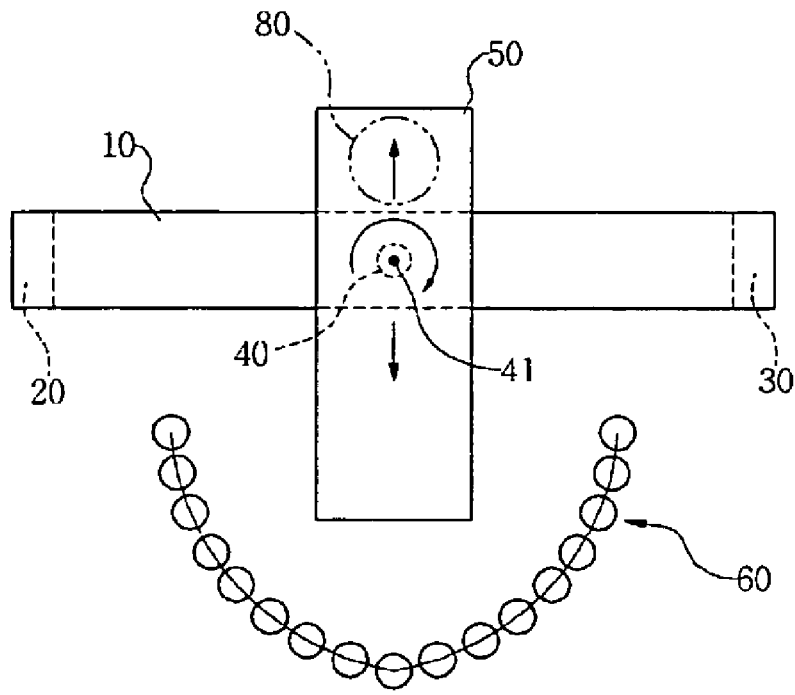
[Fig. 2]
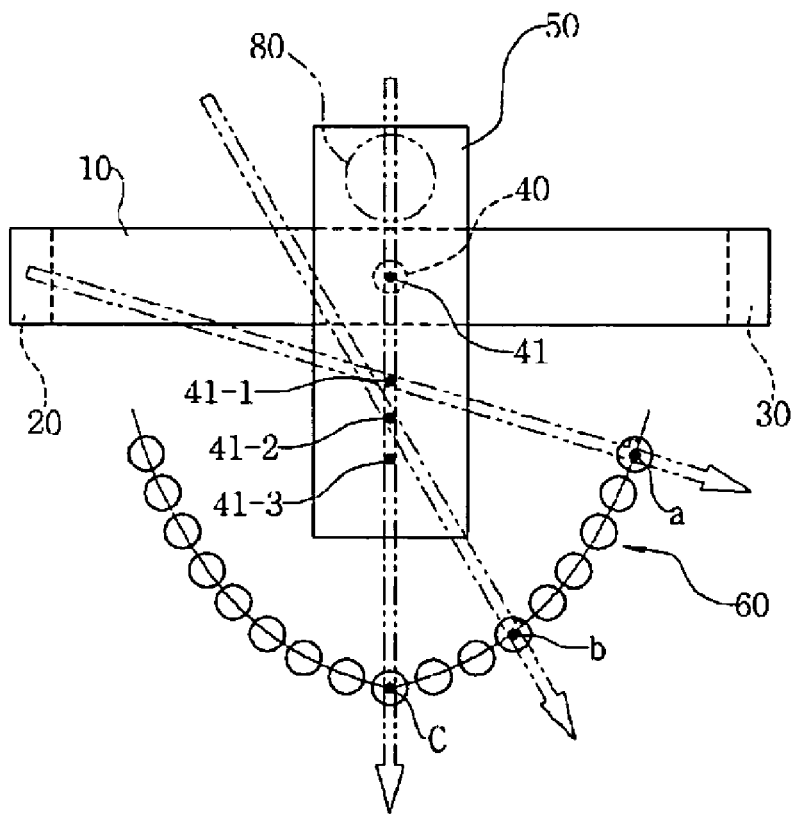

[Fig. 3]
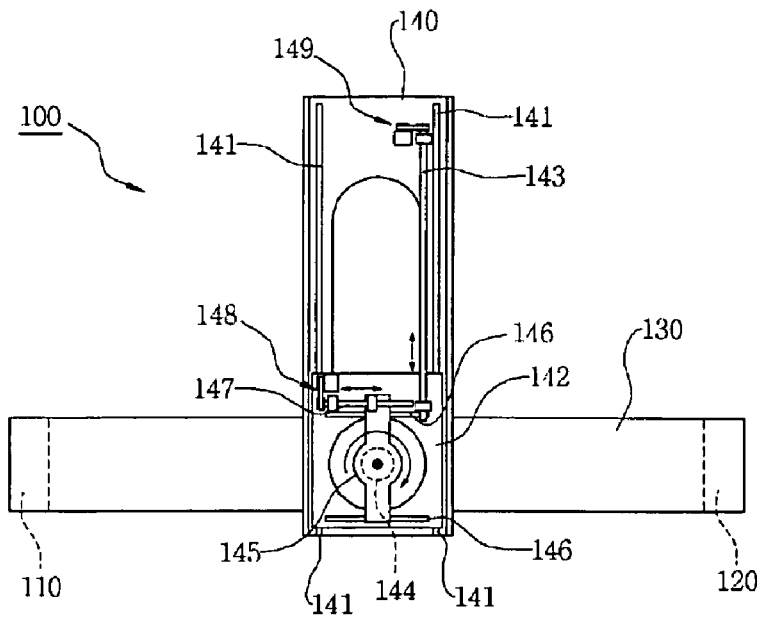
[Fig. 4]
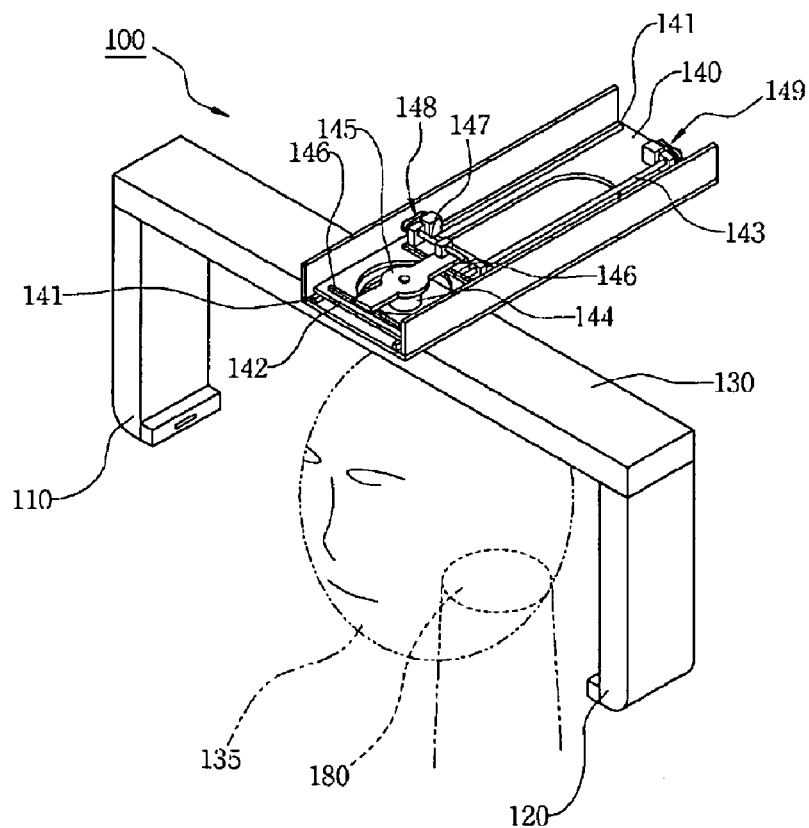

[Fig. 5]
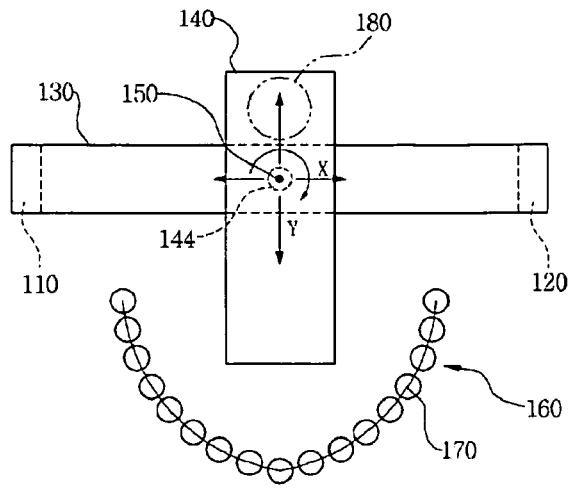
[Fig. 6]
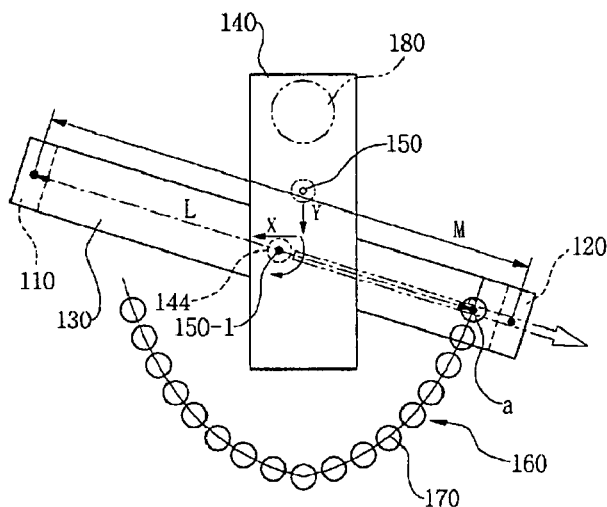
[Fig. 7]
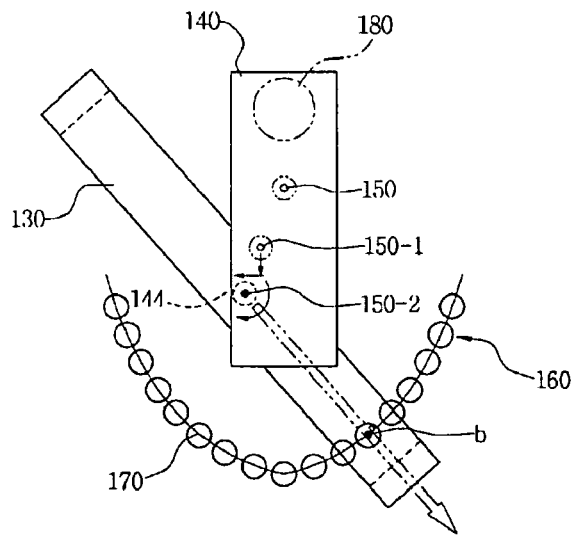

[Fig. 8]
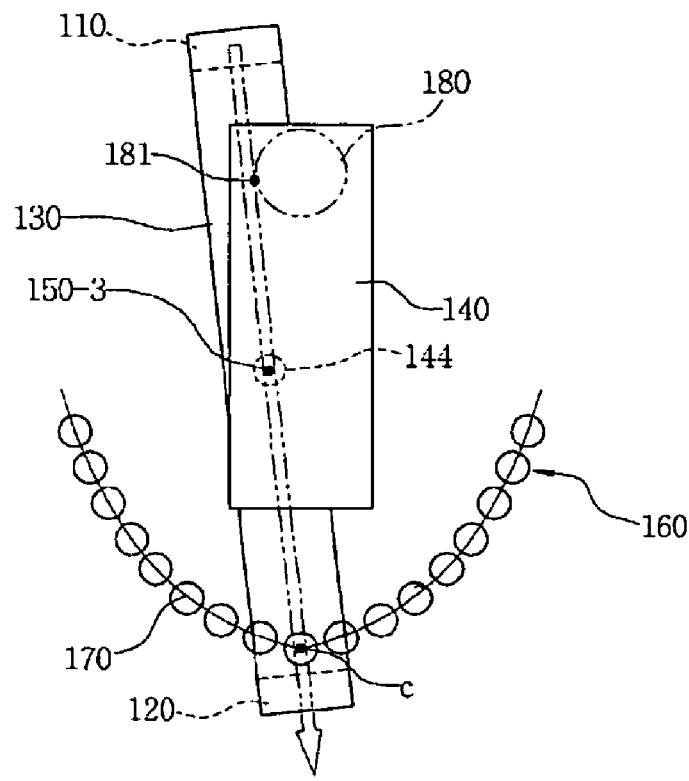
[Fig. 9]
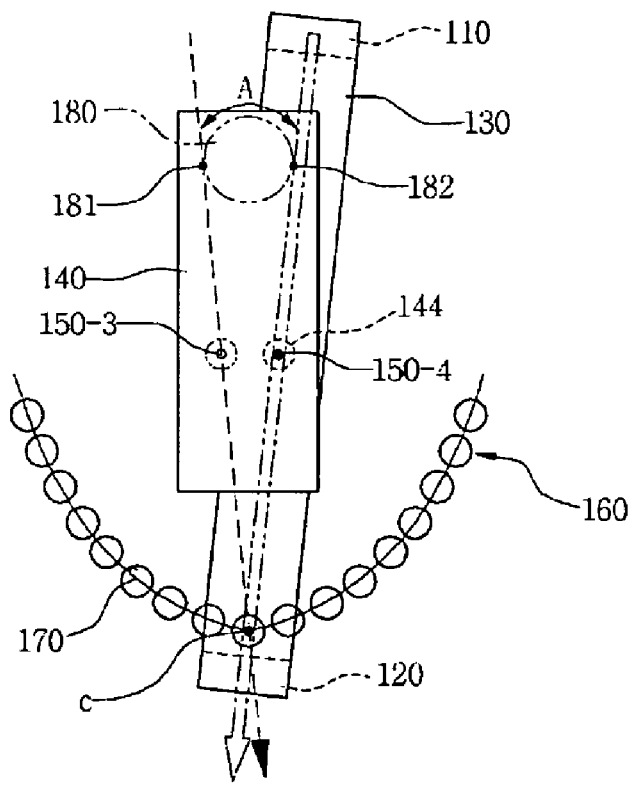

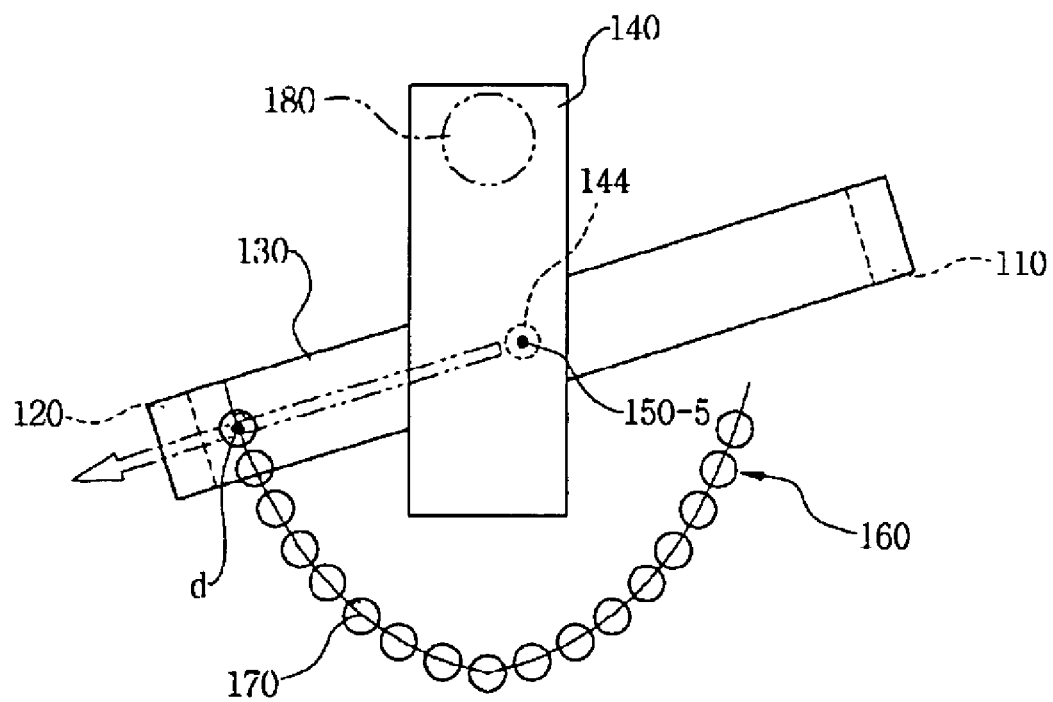
[Fig. 10]
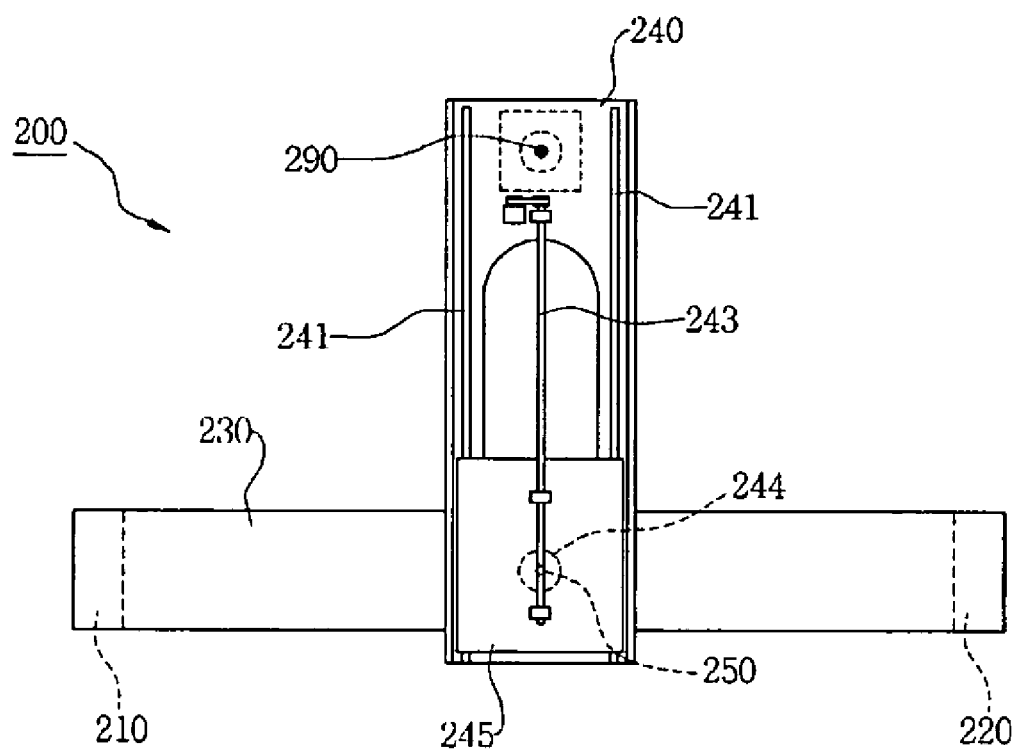
[Fig. 11]

[Fig. 12]
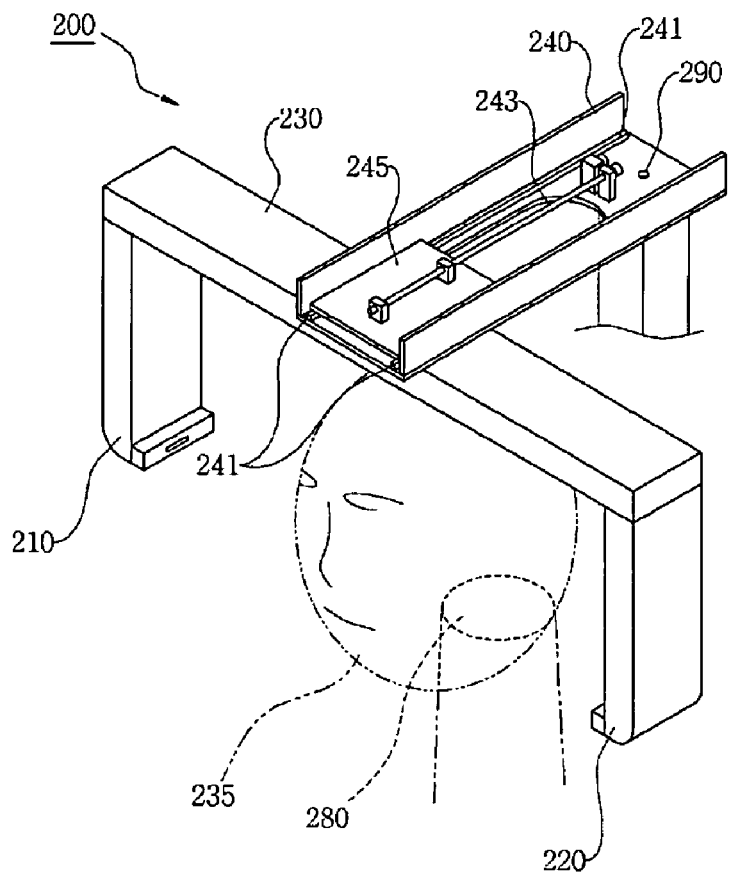
[Fig. 13]
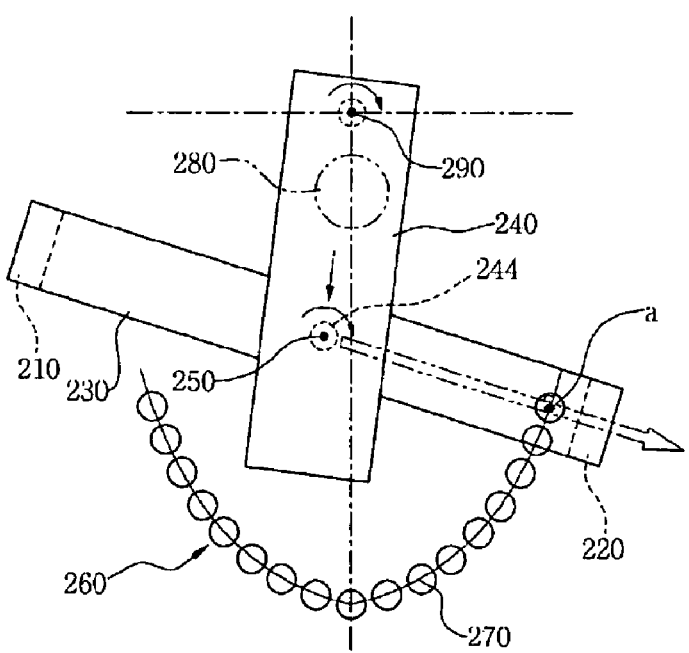

[Fig. 14]
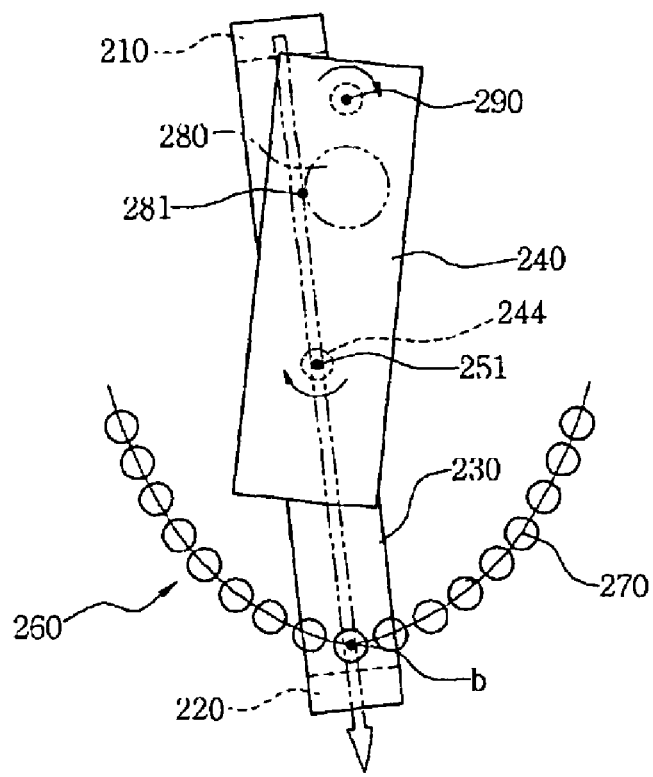
[Fig. 15]
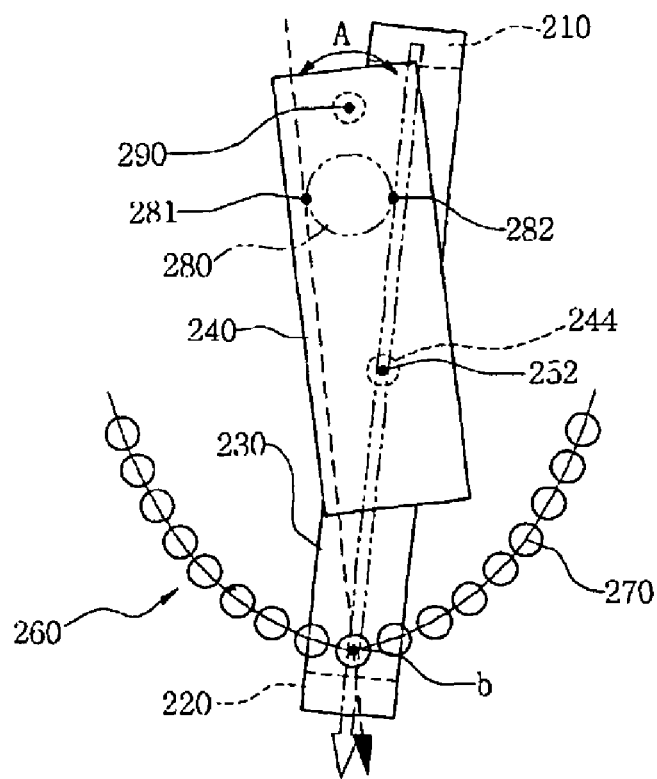

PANORAMIC X-RAY PHOTOGRAPHING APPARATUS AND METHOD FOR PHOTOGRAPHING USING THE SAME

This is a National Phase Application filed under 35 USC 371 of International Application No. PCT/KR2007/000932, filed on Feb. 22, 2007, the entire content of which is hereby incorporated by reference in its entirety.

TECHNICAL FIELD

The present invention relates to an X-ray photographing apparatus and a method for photographing using the same, more particularly, to a panoramic X-ray photographing apparatus capable of conducting a panoramic photographing without generating X-ray in neck cervical vertebrae part employing a rotary arm driven in 3-axis direction and a method for photographing the same.

BACKGROUND ART

In the field of the dental diagnosis, conventionally, an X-ray panoramic imaging apparatus takes a tomographic image along the curve of a dental arch.

FIGS. 1 and 2 show a conventional X-ray panoramic imaging apparatus.

Referring to FIG. 1, the conventional X-ray panoramic imaging apparatus 1 comprises a rotary arm including an X-ray light source part 20 and an X-ray sensor part 30, and a rotary arm supporting member 50 for supporting the rotary arm.

The rotary arm supporting member 50 includes a rotary arm driving means, thereby rotary driving the rotary arm 30 in a center of a rotary axis 41. In addition, the rotary arm 30 is linearly driven in a length direction of the rotary arm supporting member 50. That is, the conventional X-ray panoramic imaging apparatus 1 takes a photograph a dental arch 60 of a patient with rendering the rotary arm performed as linear driving and rotary driving.

Hereinafter, a method for performing a panoramic photographing employing a conventional X-ray panoramic imaging apparatus 1 will be described referring to FIG. 2.

Once photographing, the rotary arm 30 takes a photograph a photographing point (a) by performing linear driving (Y-axis driving) equivalent to a length direction of the rotary arm supporting member and rotary driving. At this time, the rotary axis 41 is moved to new rotary axis (41-1) and then, the position of the rotary axis 41 is continuously changed (from (41-2) to (41-3) to photograph the dental arch of a patient.

In case of photographing the photographing point (a), an irradiated X-ray is not met with neck cervical vertebrae part of a patient, so that an acquired image becomes clear relatively. However, it is difficult to control an incident angle at a point (a) of an object to be vertical. As a result, there is a problem that the acquired image may be distorted. Furthermore, controlling an enlargement ratio is difficult in photographing tempromandibular joint (hereinafter, referred as a TMJ).

In photographing points (b) and (c) of the object, irradiated X-ray meets neck cervical vertebrae of patient, so that an acquired image is not clear and distorted because it is difficult to render an incidence angle with respect to the photographing points (b) and (c) to be vertical.

Scanning the neck cervical vertebrae is essential in panoramic photographing. Therefore, there are many problems in that an acquired image is unclear and distorted. Controlling enlargement ratio is also difficult.

Various devices and methods for driving a rotary arm in 3-axis direction have been introduced, the above-mentioned problems remains the same.

DISCLOSURE OF INVENTION

Technical Problem

Accordingly, it is an object of the present invention to provide an X-ray photographing apparatus capable of preventing an acquired image being unclear owing to neck cervical vertebrae and a method for photographing the same.

It is another object of the present invention to provide an X-ray photographing apparatus capable of preventing a distortion of an image as well as controlling optimum enlargement in photographing neck cervical vertebrae by rendering an incidence angle of an X-ray to be vertical.

Technical Solution

To achieve the above object, the present invention provides a panoramic X-ray photographing apparatus. The panoramic X-ray photographing comprises a rotary arm for arranging an X-ray light source part and an X-ray sensor part thereon in such a way as to be opposed to each other and a rotary arm supporting member for supporting the rotary arm. The rotary arm supporting member includes a rotary driving means for rotary driving the rotary arm, a means for driving the rotary arm to a length direction (Y-axis direction) of the rotary arm supporting member, and a means for driving the rotary arm in a direction (X-axis direction) vertical to the length direction of the rotary arm supporting member.

The present invention also provides a panoramic X-ray photographing apparatus comprises a rotary arm for arranging an X-ray light source part and an X-ray sensor part thereon in such a way as to be opposed to each other; and a rotary arm supporting member for supporting the rotary arm. The rotary arm supporting member may comprise: a Y-axis LM (Linear Motion) guide disposed at both sides of the rotary arm supporting member in a Y-axis direction; a base having a hole in a center thereof and moved in the Y-axis direction on the Y-axis LM guides; a Y-axis driving means put on the base in the same direction as any one of Y-axis LM guides and rendering the base moved in the Y-axis direction; a rotary arm connecting means for connecting the rotary arm through a hole of the base and having a rotary driving means for driving the rotating the rotary arm; a X-axis LM guide disposed at both sides of the abase in a X-axis direction; and a X-axis driving means put on the base in the same direction as any one of the X-axis LM guides and rendering the rotary arm connecting means moved to the X-axis direction.

Pursuant to embodiments of the present invention, the rotary arm connecting means is moved on the X-axis LM guides to the X-axis direction and connected by the*axis driving means.

Pursuant to some embodiments of the present invention, the X-axis driving means and the Y-axis driving means are a ball screw device.

Pursuant to other embodiments of the present invention, the X-ray light source part is turned off not to generate X-ray while a line connecting the X-ray light source part and the X-ray sensor part is in contact with neck cervical vertebrae part of a patient during panoramic photographing.

Pursuant to further embodiments of the present invention, a sensor for sensing whether the line connecting the X-ray light source part and the X-ray sensor part is in contact with the neck cervical vertebrae part of a patient is further included.

To achieve the above object, the present invention provides a panoramic X-ray photographing method by driving a rotary arm for arranging an X-ray light source part and an X-ray sensor part thereon in such a way as to be opposed to each other to photograph a dental arch of a patient, wherein the rotary arm is driven as an X-axis driving, a Y-axis driving, and a rotary driving. The rotary arm scans the dental arch of the patient without irradiating an X-ray into neck cervical vertebrae part of a patient.

The present invention also provides a panoramic X-ray photographing method by driving a rotary arm for arranging an X-ray light source part and an X-ray sensor part thereon in such a way as to be opposed to each other to photograph a dental arch of a patient, the method comprising: a first step for locating the rotary arm to photograph an initial photographing point of a dental arch; a second step for scanning and photographing the rotary arm from the initial photographing point of the dental arch to an intermediate photographing point of the dental arch of an initial point where a line connecting the X-ray light source part and the X-ray sensor part is in contact with neck cervical vertebrae part of a patient with rendering the rotary arm driving as the X-axis driving, the Y-axis driving, and the rotary driving; a third step for locating the rotary arm from the initial point where the line connecting the X-ray light source part and the X-ray sensor part is in contact with the neck cervical vertebrae part of the patient to a point where the line connecting the X-ray light source part and the X-ray sensor part is not in contact with the neck cervical vertebrae part of the patient and locating the rotary arm with maintaining the intermediate photographing point of the dental arch to be a focus; and a fourth step for scanning and photographing the rotary arm from the intermediate photographing point of the dental arch to an end photographing point of the dental arch with rendering the rotary arm driving as the X-axis driving, the Y-axis driving, and the rotary driving.

Pursuant to embodiments of the present invention, in the third step, the X-ray light source part is turned off not to generate X-ray while the rotary arm is located.

Pursuant to other embodiments of the present invention, in the third step, the rotary arm is located by driving the rotary arm as the X-axis driving and the rotary driving. Pursuant to further embodiments of the present invention, an enlargement ratio means a ratio of a distance between the object and the X-ray light source part to a distance between the X-ray sensor part and the X-ray light source part. In the steps of first, second, and third, the enlargement ratio is 1:1.1 to 1:6. Preferably, the enlargement ratio is 1:1.3.

To achieve the above object, the present invention provides a panoramic X-ray photographing apparatus comprising a rotary arm for arranging an X-ray light source part and an X-ray sensor part thereon in such a way as to be opposed to each other and a rotary arm supporting member for supporting the rotary arm. The rotary arm supporting member includes a rotary driving means for rotary driving the rotary arm, and a means for driving the rotary arm to a length direction (Y-axis direction) of the rotary arm supporting member.

The present invention also provides a panoramic X-ray photographing apparatus comprising a rotary arm for arranging an X-ray light source part and an X-ray sensor part thereon in such a way as to be opposed to each other and a rotary arm supporting member for supporting the rotary arm, having a fixing rotary axis at one end thereof, and rotated in a center of the fixing rotary axis. The rotary arm supporting member comprises: a Y-axis LM (Linear Motion) guide disposed at both sides of the rotary arm supporting member in a Y-axis direction; a rotary arm connecting means moved in the Y-axis direction and rotating the rotary arm; and a Y-axis driving means put on the rotary arm connecting means in the same direction as the Y-axis LM guides and rendering the rotary arm connecting means moved to the Y-axis direction.

Pursuant to embodiments of the present invention, the Y-axis driving means may be a ball screw device.

Pursuant to some embodiments of the present invention, the X-ray light source part is turned off not to generate X-ray while a line connecting the X-ray light source part and the X-ray sensor part is in contact with neck cervical vertebrae part of a patient during panoramic photographing.

Pursuant to other embodiments of the present invention, a sensor for sensing whether the line connecting the X-ray light source part and the X-ray sensor part is in contact with the neck cervical vertebrae part of a patient may be further included.

To achieve the above object, the present invention provides a panoramic X-ray photographing method by driving a rotary arm for arranging an X-ray light source part and an X-ray sensor part thereon in such a way as to be opposed to each other to photograph a dental arch of a patient, wherein the rotary arm is driven as an X-axis driving, a first rotary driving, and a second rotary driving, and the rotary arm scans the dental arch of the patient without irradiating an X-ray into neck cervical vertebrae part of a patient.

The present invention also provides a panoramic X-ray photographing method by driving a rotary arm for arranging an X-ray light source part and an X-ray sensor part thereon in such a way as to be opposed to each other to photograph a dental arch of a patient, the method comprising: a first step for locating the rotary arm to photograph an initial photographing point of a dental arch; a second step for scanning and photographing the rotary arm from the initial photographing point of the dental arch to an intermediate photographing point of the dental arch of an initial point where a line connecting the X-ray light source part and the X-ray sensor part is in contact with neck cervical vertebrae part of a patient with rendering the rotary arm driving as a Y-axis driving and a first rotary driving together with rendering the rotary arm supporting member driving as a second rotary driving in the center of a fixing rotary axis; a third step for locating and the rotary arm supporting member and the rotary arm from the initial point where the line connecting the X-ray light source part and the X-ray sensor part is in contact with the neck cervical vertebrae part of the patient to a point where the line connecting the X-ray light source part and the X-ray sensor part is not in contact with the neck cervical vertebrae part of the patient and locating the rotary arm with maintaining the intermediate photographing point of the dental arch to be a focus; and a fourth step for scanning and photographing the rotary arm from the intermediate photographing point of the dental arch to an end photographing point of the dental arch with rendering the rotary arm driving as the Y-axis driving and the first rotary driving together with rendering the rotary arm supporting member driving as a second rotary driving in a center of the fixing rotary axis.

Pursuant to embodiments of the present invention, in the third step, the X-ray light source part is turned off not to generate X-ray while the rotary arm is located.

Pursuant to some embodiments of the present invention, in the third step, the rotary arm is located by driving the rotary arm supporting member as the second driving in the center of the fixing rotary axis together with driving the rotary arm as the Y-axis driving.

Pursuant to other embodiments of the present invention, in the third step, the rotary arm is located by driving the rotary arm supporting member as the second driving in the center of the fixing rotary axis together with driving the rotary arm as the Y-axis driving.

Pursuant to further embodiments of the present invention, an enlargement ratio means a ratio of a distance between the object and the X-ray light source part to a distance between the X-ray sensor part and the X-ray light source part, and in the steps of first, second, and third, the enlargement ratio is 1:1.1 to 1:6. Preferably, the enlargement ratio is 1:1.3.

ADVANTAGEOUS EFFECTS

The panoramic X-ray photographing apparatus according to the present invention performs photographing without X-ray to prevent an acquired image being unclear.

Additionally, an X-ray photographing apparatus is capable of preventing a distortion of an image as well as controlling optimum enlargement in photographing neck cervical vertebrae by rendering an incidence angle of an X-ray to be vertical.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

BRIEF DESCRIPTION OF THE DRAWINGS

FIGS. 1 and 2 show a panoramic X-ray photographing apparatus according to a conventional art.

FIGS. 3 and 4 are a plane view and a perspective view for showing a panoramic X-ray photographing apparatus according to the first embodiment of the present invention.

FIGS. 5 to 10 illustrate a method for photographing using a panoramic X-ray photographing apparatus according to a first embodiment of the present invention.

FIGS. 11 and 12 are a plane view and a perspective view for showing a panoramic X-ray photographing apparatus according to the second embodiment of the present invention.

FIGS. 13 to 15 illustrate a method for photographing using a panoramic X-ray photographing apparatus according to a second embodiment of the present invention.

EXPLANATION ON ESSENTIAL REFERENCE NUMERALS IN DRAWINGS 100,200: panoramic X-ray photographing apparatus
110,210: X-ray light source part
120,220: X-ray sensor part
130,230: rotary arm
140,240: rotary arm supporting member
150,250: rotary axis
160: dental arch
170,270: photographing track
180,280: neck cervical vertebrae
290: fixing rotary axis
141,241: Y-axis LM guide
142: base
143,243: Y-axis driving means
144,244: rotary arm driving means
145,245: rotary arm connecting means
146: X-axis LM guide
147: X-axis driving means

BEST MODE FOR CARRYING OUT THE INVENTION

Reference will now be made in detail to the preferred embodiments of the present invention, examples of which are illustrated in the accompanying drawings. The present invention is not restricted to the embodiments of the present invention but can be embodied in other various forms. The same reference numerals designate the same parts in the present invention.

FIGS. 3 and 4 are a plane view and a perspective view for showing a panoramic X-ray photographing apparatus according to the first embodiment of the present invention Referring to FIGS. 3 and 4, the X-ray panoramic apparatus 100 includes an X-ray light source part 110, a rotary arm 130 including an X-ray sensor part 120, and a rotary arm supporting member 140 for supporting the rotary arm 130.

The X-ray light source part 110 and the X-ray sensor part 120 are opposed each other. The rotary arm 130 rotates a circumference of an object 135 and is driven in a rectilinear direction to perform a panoramic photographing. The rectilinear driving means a driving in a length direction of the rotary arm supporting member 140 (hereinafter, referred to as Y-axis driving) and a driving in a direction vertical to the length direction of the rotary arm supporting member 140 (hereinafter, referred to as X-axis driving).

In the first embodiment, a panoramic photographing is performed in rendering the rotary arm 130 driving as X-axis driving, Y-axis driving, and rotary driving. Accordingly, a structure that is capable of preventing an acquired image from being unclear by scanning neck cervical vertebrae of the object 135 is suggested. Moreover, a structure that is capable of easily controlling an enlargement and minimizing load with respect to a motor 149 in rendering an incidence angle of X-ray to be vertical is suggested.

In more detail, the rotary arm supporting member 140 is formed so as to support the rotary arm 130 as well as rendering the rotary 130 driving as X-axis driving, Y-axis driving, and rotary driving.

In advance, Y-axis LM guides 141 are disposed at both sides of the rotary arm supporting member 140 in Y-axis direction, respectively. On the Y-axis LM guide 141, a base 142 is disposed. The base 142 is slid on the Y-axis LM guide 141 to be moved toward Y-axis direction.

A hole connecting the rotary arm 130 is formed on the base 142. And, a Y-axis driving means 143, an X-axis LM guide 146, and an X-axis driving means 147 are formed. At this time, the Y-axis LM guide 141 and the Y-axis driving means 143, and the X-axis LM guide 146 and the X-axis driving means 147 are arranged in the same direction in a line.

A part of the Y-axis driving means 143 stretches on the base 142 and drives the base 142 toward the Y-axis direction on the Y-axis LM guide 141. In the first embodiment of the present invention, a ball screw device as the Y-axis driving means 143 are formed. Thus, the base 142 is driven in the Y-axis direction by the motor 149. Various devices are applicable as the Y-axis driving means 143.

The X-axis LM guides 146 are formed at both up and down sides of the base 142. On any upper portion of the X-axis LM guide 146, the X-axis driving means 147 are arranged in the same direction in a line.

A rotary arm connecting means 145 is disposed on the X-axis LM guide 146 and slid to be moved toward X-axis. A part of the rotary arm connecting means 145 is connected to the X-axis driving means 147 to be driven in the X-axis direction. In this case, a ball screw device as the X-axis driving means 147 is formed. As a result, the rotary arm connecting means 145 is driven in the X-axis direction by the motor 148.

The rotary arm connecting means 145 connects the rotary arm 130 through a hole of the base 142 and includes the rotary arm driving means 144 for driving the rotary arm 130.

In accordance with these structures, the rotary arm 130 is driven as X-axis driving, Y-axis driving, and the rotary driving. In addition, the rotary arm 130 can be driven as the X-axis driving and the rotary driving, and the rotary driving and Y-axis driving, and X-axis driving, Y-axis driving, the rotary driving, at the same time.

The X-ray light source part 110 is turned off not to generate X-ray while a line connecting the X-ray light source part 110 and the X-ray sensor part 120 is in contact with neck cervical vertebrae part 180 of a patient during panoramic photographing.

As not shown, the panoramic X-ray photographing apparatus 100 includes a sensor for sensing whether the line connecting the X-ray light source part 110 and the X-ray sensor part 120 is in contact with neck cervical vertebrae part 180 of a patient. In the event that the line connecting the X-ray light source part 110 and the X-ray sensor part 120 is in contact with neck cervical vertebrae part 180 of a patient, the sensor senses and transmits it to a central processing device. The central processing device turns off the X-ray light source part 110 not to generate X-ray while receiving a signal from the sensor. The sensor may be an infrared sensor and disposed at a predetermined region of the X-ray light source part 110.

The panoramic photographing will be described in more detail hereinafter.

FIGS. 5 to 10 illustrate a method for photographing using a panoramic X-ray photographing apparatus according to a first embodiment of the present invention.

Referring to FIGS. 5 and 6, the rotary arm 130 includes the X-ray light source part 110 and the X-ray sensor part 120, which are opposed to each other. The rotary arm 130 is supported by the rotary arm supporting member 140.

As shown in FIGS. 3 and 4, the rotary arm 130 may be rotated in the center of a rotary axis 150 and at the same time, driven as the X-axis driving and Y-axis driving via an internal structure of the rotary arm supporting member 140.

At this time, neck cervical vertebrae are always included in a track of the rotary arm 130.

Once panoramic photographing, the rotary arm 130 is moved to a position in which an initial photographing point (a) of a dental arch 160 is scanned. That is, the rotary arm 130 is driven as the rotary driving together with the X-axis driving and the Y-axis driving and then moved toward the initial photographing point (a).

At this time, a first position 150 is moved to a second position (150-1). The reason for this is to photograph in a conformal enlargement since TMJ is essentially photographed in photographing the initial photographing point (a). Additionally, an incidence angle of X-ray with respect to the initial photographing point (a) is vertical to prevent the distortion of an image.

The enlargement ratio means a ratio of a distance (L) between the object 135 and the X-ray light source part 110 to a distance (M) between the X-ray sensor part 120 and the X-ray light source part 110. The higher enlargement is, the higher an acquired image is. High enlargement is harmful to patient because of a large amount of X-ray. If the enlargement is low, it is difficult to manufacture the panoramic X-ray photographing apparatus. Thus, it is preferable that photographing is performed by employing optimum enlargement ratio in order to obtain desirable image or easily manufacture photographing apparatus. Preferably, the enlargement ratio is 1:1.1 to 1:6. It is most preferable that panoramic photographing is performed by employing the enlargement ratio is 1:1.3

Referring to FIGS. 7 and 8, panoramic photographing is continuously performed along a photographing track from the initial photographing point (a) to the photographing points (b) and (c). In other words, from the initial photographing point (a) to the intermediate photographing point (c) being a point equivalent to a line connecting the X-ray light source part 110 and the X-ray sensor part 120 in contact with the neck cervical vertebrae 180 of patients, an image is obtained by rendering the rotary arm driving as the X-axis driving, the Y-axis driving, and the rotary driving. In this case, the rotary axis is continuously moved from a third position (150-2) to a fourth position (150-3).

Referring to FIGS. 9 and 10, a method for photographing a part (A) in which the line connecting the X-ray light source part 110 and the X-ray sensor part 120 passes the neck cervical vertebrae 180 of patients is illuminated.

From the point 181 where the line connecting the X-ray light source part 110 and the X-ray sensor part 120 in contact with the neck cervical vertebrae 180 of patients to a point 182 where the line not in contact with the neck cervical vertebrae 180 of patients, the rotary arm 130 is located by the X-axis driving and the rotary driving. In maintaining a focus of the panoramic photographing as the intermediate photographing point (c), the rotary axis is moved from the third position (150-2) to the fourth position (150-3).

At this time, the X-ray light source part 100 is turned off not to generate X-ray in the part (A) in which the line connecting the X-ray light source part 110 and the X-ray sensor part 120 passes the neck cervical vertebrae 180 of patients. Resultantly, it is possible to obtain clear image by excluding an image of neck cervical vertebrae 180 of patients.

In case that the line connecting the X-ray light source part 110 and the X-ray sensor part 120 passes the neck cervical vertebrae 180 of patients, various methods for retraining X-ray can be used. As mentioned above, an infrared sensor can be adopted, and X-ray is controlled by data-basing a distance or a location between dental arch and neck cervical vertebrae. That is, if the line for connecting the X-ray light source part 110 and the X-ray sensor part 120 is recognized as passing neck cervical vertebrae by previous input data, X-ray is not generated.

Continuously, from the intermediate photographing point (c) to end photographing point (d), all panoramic images are obtained by panoramic photographing with rendering the rotary arm 130 as X-axis driving, Y-axis driving, and rotary driving (the rotary axis is moved to (150-5)).

MODE FOR THE INVENTION

FIGS. 11 and 12 are a plane view and a perspective view for showing a panoramic X-ray photographing apparatus according to the second embodiment of the present invention.

Referring to FIGS. 11 and 12, a panoramic X-ray photographing apparatus 200 according to the second embodiment of the present invention includes an X-ray light source part 210, a rotary arm 230 including an X-ray sensor part 220, and a rotary arm supporting member 240 including a fixing rotary axis at one end thereof and driven as a second rotary driving in a center of the fixing rotary axis 290.

The X-ray light source part 210 is opposed to the X-ray sensor part 220 to each other. The rotary arm 130 is drive as a first rotary driving at a circumference of an object 235 and is driven in a rectilinear direction to perform a panoramic photographing. The rectilinear driving means a driving in a length direction of the rotary arm supporting member 240 (hereinafter, referred to as Y-axis driving).

In the second embodiment, a panoramic photographing is performed in rendering the rotary arm 230 driving as Y-axis driving, and a first rotary driving. Accordingly, a structure that is capable of preventing an acquired image from being unclear by scanning neck cervical vertebrae of the object 135 is suggested. Moreover, a structure that is capable of easily controlling an enlargement and minimizing load with respect to a motor in rendering an incidence angle of X-ray to be vertical is suggested.

In more detail, the rotary arm supporting member 240 is formed to support the rotary arm 230 as well as render the rotary arm driving as Y-axis driving and the first rotary driving.

A Y-axis LM guide 241 is formed at both sides of the rotary arm supporting member 240 in a Y-axis direction. A rotary arm connecting means 245 is formed on the Y-axis LM guide 241. The rotary arm connecting means 245 is slid on the Y-axis LM guide 241 to be moved toward the Y-axis direction.

The rotary arm connecting means 245 includes a rotary arm driving means 244 for rendering the rotary arm 230 as a first rotary driving.

The Y-axis driving means 243 is arranged in the same direction as the Y-axis LM guide 241 in a line. A part of the Y-axis driving means 243 stretches on the rotary arm connecting means 245. The Y-axis driving means 243 drives the rotary arm connecting means 245 on the Y-axis LM guide 241 toward the Y-axis direction. In this case, a ball screw device as the Y-axis driving means 243 is formed.

The rotary arm 230 may be driven as Y-axis driving, the first rotary driving, and the second rotary driving of the rotary arm supporting member 240, respectively or simultaneously.

The X-ray light source part 210 is turned off not to generate X-ray while a line for connecting the X-ray light source part 210 and the X-ray sensor part 220 is in contact with an object 235 being neck cervical vertebrae 280 of a patient.

As not shown, the panoramic X-ray apparatus 200 includes an infrared sensor for sensing whether the line for connecting the X-ray light source part 210 and the X-ray sensor part 220 is in contact with an object 235 being neck cervical vertebrae 280 of a patient.

Panoramic photographing will be described hereinafter.

FIGS. 13 to 15 illustrate a method for photographing using a panoramic X-ray photographing apparatus according to a second embodiment of the present invention.

Referring to FIG. 13, the rotary arm 230 includes the X-ray light source part 210 and the X-ray sensor part 220, which are opposed to each other. The rotary arm 230 is supported by the rotary arm supporting member 240.

The rotary arm 230, as shown in FIGS. 11 and 12, is driven as the Y-axis driving and the first rotary driving through an internal structure of the rotary arm supporting member 240. In addition, the rotary arm 230 may be driven as a second rotary driving by the rotary arm supporting member 240 that is driven as the second rotary driving in the center of the fixing rotary axis 290.

In this case, it is known that the neck cervical vertebrae 280 of patients are always included in a track of the rotary arm 230.

Once starting panoramic photographing, the rotary arm 230 is moved to a predetermined position for scanning an initial photographing point (a) of a photographing track 270. That is, the rotary arm 230 is driven as the Y-axis driving together with the first and second driving to be moved to the initial photographing point (a) of the photographing track 270.

The location of a rotary axis of the first rotary driving is continuously changed from a first position 250, and a rotary axis of the second rotary driving is fixed by the fixing rotary axis 290. The reason for this is to photograph in a conformal enlargement since TMJ is essentially photographed in photographing the initial photographing point (a). Additionally, an incidence angle of X-ray with respect to the initial photographing point (a) is vertical to prevent the distortion of an image.

The enlargement ratio can be controlled in the second embodiment of the present invention. To avoid descriptive duplication, accordingly, the explanation thereof will be omitted herein.

Referring to FIGS. 14 and 15, a method for photographing a part (A) in which the line connecting the X-ray light source part 210 and the X-ray sensor part 220 passes the neck cervical vertebrae 280 of patients is illuminated.

From the point 281 where the line connecting the X-ray light source part 210 and the X-ray sensor part 220 in contact with the neck cervical vertebrae 180 of patients to a point 282 where the line not in contact with the neck cervical vertebrae 180 of patients, the rotary arm 230 is located by the X-axis driving and the rotary driving. That is, the rotary arm supporting member 240 is driven as a second rotary driving, and the rotary arm 230 is driven as a first rotary driving to be located. In maintaining a focus of the panoramic photographing as the intermediate photographing point (b), the rotary axis is moved from a second position (251) to a third position (252).

At this time, the X-ray light source part 210 is turned off not to generate X-ray in the part (A) in which the line connecting the X-ray light source part 210 and the X-ray sensor part 220 passes the neck cervical vertebrae 280 of patients. Resultantly, it is possible to obtain clear image by excluding an image of neck cervical vertebrae 280 of patients.

Continuously, from the intermediate photographing point (b) to end photographing point (d), all panoramic images are obtained by panoramic photographing with rendering the rotary arm 230 as Y-axis driving and the first rotary driving, and rendering the rotary arm supporting member 240 as the second rotary driving.

Except above-mentioned description, the panoramic X-ray apparatus and the photographing method are the same as described in the first embodiment of the present invention.

INDUSTRIAL APPLICABILITY

The present invention relates to panoramic X-ray apparatus and a method for photographing using the same. The present invention can be employed in various fields such as the medical diagnosis and dental diagnosis. According to the present invention, a photographing can be conduct without generating X-ray in scanning neck cervical vertebrae, In addition, the panoramic X-ray apparatus is capable of preventing a distortion of an image as well as controlling optimum enlargement in photographing neck cervical vertebrae by rendering an incidence angle of an X-ray to be vertical, so that clear image can be obtained.

The invention claimed is:

1. A panoramic X-ray photographing apparatus comprising:
   a rotary arm for arranging an X-ray light source part and an X-ray sensor part thereon in such a way as to be opposed to each other; and
   a rotary arm supporting member for supporting the rotary arm, wherein the rotary arm supporting member comprises:
   a Y-axis LM (Linear Motion) guide disposed at both sides of the rotary arm supporting member in a Y-axis direction;
   a base having a hole in a center thereof and moved in the Y-axis direction on the Y-axis LM guides;
   a Y-axis driving means put on the base in the same direction as any one of Y-axis LM guides and rendering the base moved in the Y-axis direction;
   a rotary arm connecting means for connecting the rotary arm through a hole of the base and having a rotary driving means for driving the rotating the rotary arm;
   a X-axis LM guide disposed at both sides of the abase in a X-axis direction; and
   X-axis driving means put on the base in the same direction as any one of the X-axis LM guides and rendering the rotary arm connecting means moved to the X-axis direction.

2. The panoramic X-ray photographing apparatus according to claim 1, wherein the rotary arm connecting means is moved on the X-axis LM guides to the X-axis direction and connected by the-X-axis driving means.

3. The panoramic X-ray photographing apparatus according to claim 1, wherein the X-axis driving means and the Y-axis driving means are a ball screw device.

4. The panoramic X-ray photographing apparatus according to claim 1, wherein the X-ray light source part is turned off not to generate X-ray while the line connecting the X-ray light source part and the X-ray sensor part is in contact with the neck cervical vertebrae part of a patient during panoramic photographing.

5. The panoramic X-ray photographing apparatus according to claim 4, further comprising a sensor for sensing whether the line connecting the X-ray light source part and the X-ray sensor part is in contact with the neck cervical vertebrae part of a patient.

6. A panoramic X-ray photographing method by driving a rotary arm for arranging an X-ray light source part and an X-ray sensor part thereon in such a way as to be opposed to each other to photograph a dental arch of a patient, the method comprising:
   a first step for locating the rotary arm to photograph an initial photographing point of a dental arch;
   a second step for scanning and photographing the rotary arm from the initial photographing point of the dental arch to an intermediate photographing point of the dental arch of an initial point where a line connecting the X-ray light source part and the X-ray sensor part is in contact with neck cervical vertebrae part of a patient with rendering the rotary arm driving as the X-axis driving, the Y-axis driving, and the rotary driving;
   a third step for locating the rotary arm from the initial point where the line connecting the X-ray light source part and the X-ray sensor part is in contact with the neck cervical vertebrae part of the patient to a point where the line connecting the X-ray light source part and the X-ray sensor part is not in contact with the neck cervical vertebrae part of the patient and locating the rotary arm with maintaining the intermediate photographing point of the dental arch to be a focus; and
   a fourth step for scanning and photographing the rotary arm from the intermediate photographing point of the dental arch to an end photographing point of the dental arch with rendering the rotary arm driving as the X-axis driving, the Y-axis driving, and the rotary driving.

7. The method according to claim 6, in the third step, wherein the X-ray light source part is turned off not to generate X-ray while the rotary arm is located.

8. The method according to claim 7, in the third step, wherein the rotary arm is located by driving the rotary arm as the X-axis driving and the rotary driving.

9. The method according to claim 8, wherein an enlargement ratio means a ratio of a distance between the object and the X-ray light source part to a distance between the X-ray sensor part and the X-ray light source part, and wherein in the steps of first, second, and third, the enlargement ratio is 1:1.1 to 1:6.

10. The method according to claim 9, wherein the enlargement ratio is 1:1.3.

11. A panoramic X-ray photographing apparatus comprising:
    a rotary arm for arranging an X-ray light source part and an X-ray sensor part thereon in such a way as to be opposed to each other to photograph a dental arch of a patient; and
    a rotary arm supporting member for supporting the rotary arm, having a fixing rotary axis at one end thereof, and rotated in a center of the fixing rotary axis, wherein the rotary arm supporting member comprises:
    a Y-axis LM (Linear Motion) guide disposed at both sides of the rotary arm supporting member in a Y-axis direction to drive the rotary arm from an intermediate photographing point of the dental arch to an end photographing point of the dental arch;
    a rotary arm connecting means moved in the Y-axis direction and rotating the rotary arm; and
    a Y-axis driving means put on the rotary arm connecting means in the same direction as the Y-axis LM guides and rendering the rotary arm connecting means moved to the Y-axis direction, and
    wherein the rotary arm is driven along the Y-axis and rotated about a rotary axis and the rotary arm supporting member is rotated about the fixing rotary axis, from an initial photographing point of the dental arch to an intermediate photographing point of the dental arch where a line connecting the X-ray light source part and the X-ray sensor part is in contact with neck cervical vertebrae part of a patient,
    the rotary arm and the rotary arm supporting member are moved from the initial point where the line connecting the X-ray light source part and the X-ray sensor part is in contact with the neck cervical vertebrae part of the patient to a point where the line connecting the X-ray light source part and the X-ray sensor part is not in contact with the neck cervical vertebrae part of the patient with maintaining the intermediate photographing point of the dental arch to be a focus, and
    the rotary arm is driven along the Y-axis and rotated about a rotary axis and the rotary arm supporting member is rotated about the fixing rotary axis, from the intermediate photographing point to an end photographing point of the dental arch.

12. The panoramic X-ray photographing apparatus according to claim 11, wherein the Y-axis driving means is a ball screw device.

13. The panoramic X-ray photographing apparatus according to claim 11, wherein the X-ray light source part is turned off not to generate X-ray while a line connecting the X-ray light source part and the X-ray sensor part is in contact with neck cervical vertebrae part of a patient during panoramic photographing.

14. The panoramic X-ray photographing apparatus according to claim 11, wherein the X-ray light source part is turned off not to generate X-ray while the line connecting the X-ray light source part and the X-ray sensor part is in contact with the neck cervical vertebrae part of a patient during panoramic photographing.

15. The panoramic X-ray photographing apparatus according to claim 13, further comprising a sensor for sensing whether the line connecting the X-ray light source part and the X-ray sensor part is in contact with the neck cervical vertebrae part of a patient.

16. The panoramic X-ray photographing apparatus according to claim 14, further comprising a sensor for sensing whether the line connecting the X-ray light source part and the X-ray sensor part is in contact with the neck cervical vertebrae part of a patient.

17. A panoramic X-ray photographing method by driving a rotary arm for arranging an X-ray light source part and an X-ray sensor part thereon in such a way as to be opposed to each other to photograph a dental arch of a patient, the method comprising:
  a first step for locating the rotary arm to photograph an initial photographing point of a dental arch;
  a second step for scanning and photographing the rotary arm from the initial photographing point of the dental arch to an intermediate photographing point of the dental arch of an initial point where a line connecting the X-ray light source part and the X-ray sensor part is in contact with neck cervical vertebrae part of a patient with rendering the rotary arm driving as a Y-axis driving and a first rotary driving together with rendering the rotary arm supporting member driving as a second rotary driving in the center of a fixing rotary axis;
  a third step for locating and the rotary arm supporting member and the rotary arm from the initial point where the line connecting the X-ray light source part and the X-ray sensor part is in contact with the neck cervical vertebrae part of the patient to a point where the line connecting the X-ray light source part and the X-ray sensor part is not in contact with the neck cervical vertebrae part of the patient and locating the rotary arm with maintaining the intermediate photographing point of the dental arch to be a focus; and
  a fourth step for scanning and photographing the rotary arm from the intermediate photographing point of the dental arch to an end photographing point of the dental arch with rendering the rotary arm driving as the Y-axis driving and the first rotary driving together with rendering the rotary arm supporting member driving as a second rotary driving in a center of the fixing rotary axis.

18. The method according to claim 17, in the third step, wherein the X-ray light source part is turned off not to generate X-ray while the rotary arm is located.

19. The method according to claim 18, in the third step, wherein the rotary arm is located by driving the rotary arm supporting member as the second driving in the center of the fixing rotary axis together with driving the rotary arm as the Y-axis driving.

20. The method according to claim 19, wherein an enlargement ratio means a ratio of a distance between the object and the X-ray light source part to a distance between the X-ray sensor part and the X-ray light source part, and wherein in the steps of first, second, and third, the enlargement ratio is 1:1.1 to 1:6.

21. The method according to claim 20, wherein the enlargement ratio is 1:1.3.

* * * * *